US011278729B2

(12) United States Patent
Unterweissacher et al.

(10) Patent No.: US 11,278,729 B2
(45) Date of Patent: Mar. 22, 2022

(54) INDUCTIVE LINK COUPLING BASED ON RELATIVE ANGULAR POSITION DETERMINATION FOR MEDICAL IMPLANT SYSTEMS

(71) Applicant: MED-EL Elektromedizinische Geraete GmbH, Innsbruck (AT)

(72) Inventors: Martin Unterweissacher, Innsbruck (AT); Aitor Morillo, Innsbruck (AT); Stefan Strasser, Buch in Tirol (AT); Angelo De Marzo, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 137 days.

(21) Appl. No.: 16/759,800

(22) PCT Filed: Nov. 19, 2018

(86) PCT No.: PCT/US2018/061740
§ 371 (c)(1),
(2) Date: Apr. 28, 2020

(87) PCT Pub. No.: WO2019/099969
PCT Pub. Date: May 23, 2019

(65) Prior Publication Data
US 2020/0330775 A1 Oct. 22, 2020

Related U.S. Application Data

(60) Provisional application No. 62/588,454, filed on Nov. 20, 2017.

(51) Int. Cl.
*A61N 1/372* (2006.01)
*A61N 1/36* (2006.01)
(Continued)

(52) U.S. Cl.
CPC ....... *A61N 1/37217* (2013.01); *A61N 1/0541* (2013.01); *A61N 1/36038* (2017.08);
(Continued)

(58) Field of Classification Search
CPC ..................... A61N 1/37229; A61N 1/3787
See application file for complete search history.

(56) References Cited

U.S. PATENT DOCUMENTS 7,225,028 B2 * 5/2007 Della Santina ........ A61N 1/372
607/57
9,144,677 B2 * 9/2015 Garnham ............. A61B 5/6817
(Continued)

FOREIGN PATENT DOCUMENTS

| WO | WO 2012/012634 A1 | 1/2012 |
|---|---|---|
| WO | WO 2013/134873 A1 | 9/2013 |
| WO | WO 2016/110783 A1 | 7/2016 |

OTHER PUBLICATIONS

International Search Authority/European Patent Office, International Search Report and Written Opinion of the International Searching Authority, Application No. PCT/US2018/061740, dated Mar. 20, 2019, 16 pages.
(Continued)

*Primary Examiner* — Eric D. Bertram
(74) *Attorney, Agent, or Firm* — Sunstein LLP (57) ABSTRACT

A portion of a vestibular prosthesis system is described which includes an external coil housing and an external holding magnet that allow rotation of the external coil housing around a rotation axis that passes through the external holding magnet orthogonal to a skin interface surface. An external communications coil arrangement within the housing includes three or more external coil segments rotationally adjacent to each other around the rotation axis, each external coil segment being independently operable by an external signal processor for coupling
(Continued)

an implant communication signal. And the external signal processor is configured to periodically operate the external coil segments to quantify rotation of the external coil housing and adjust the signal component of the implant communication signal to offset quantified rotation of the housing.

18 Claims, 4 Drawing Sheets

(51) Int. Cl.
*A61N 1/05* (2006.01)
*A61N 1/378* (2006.01)
*H04R 25/00* (2006.01)

(52) U.S. Cl.
CPC ....... *A61N 1/3787* (2013.01); *A61N 1/37229* (2013.01); *H04R 25/554* (2013.01)

(56) References Cited

U.S. PATENT DOCUMENTS

| | | | |
|---|---|---|---|
| 9,339,649 B2* | 5/2016 | Cushing | A61N 1/36038 |
| 9,872,993 B2* | 1/2018 | Zimmerling | A61N 1/37229 |
| 10,661,084 B2* | 5/2020 | Van den Heuvel | A61N 1/0541 |
| 2005/0075698 A1* | 4/2005 | Phillips | A61N 1/3787 607/61 |
| 2007/0208403 A1* | 9/2007 | Della Santina | A61N 1/372 607/137 |
| 2012/0277835 A1* | 11/2012 | Della Santina | A61N 1/36 607/62 |

OTHER PUBLICATIONS

Jack DiGiovanna et al., *Alignment of angular velocity sensors for a vestibular prosthesis*, Journal of Neuroengineering and Rehabilitation, vol. 9, No. 1, Jan. 1, 2012, 13 pages.

Dai Jiang et al., *Vestibular prosthesis design for restoring balance*, Analog Integrated Circuits and Signal Processing, vol. 77, No. 3, Oct. 9, 2013, pp. 319-332.

* cited by examiner

INDUCTIVE LINK COUPLING BASED ON RELATIVE ANGULAR POSITION DETERMINATION FOR MEDICAL IMPLANT SYSTEMS

This application claims priority from U.S. Provisional Patent Application 62/588,454, filed Nov. 20, 2017, which is incorporated herein by reference in its entirety.

TECHNICAL FIELD

The present invention relates to implantable stimulation systems, and more specifically to a vestibular implant system with external motion sensors.

BACKGROUND ART

Figure 1:
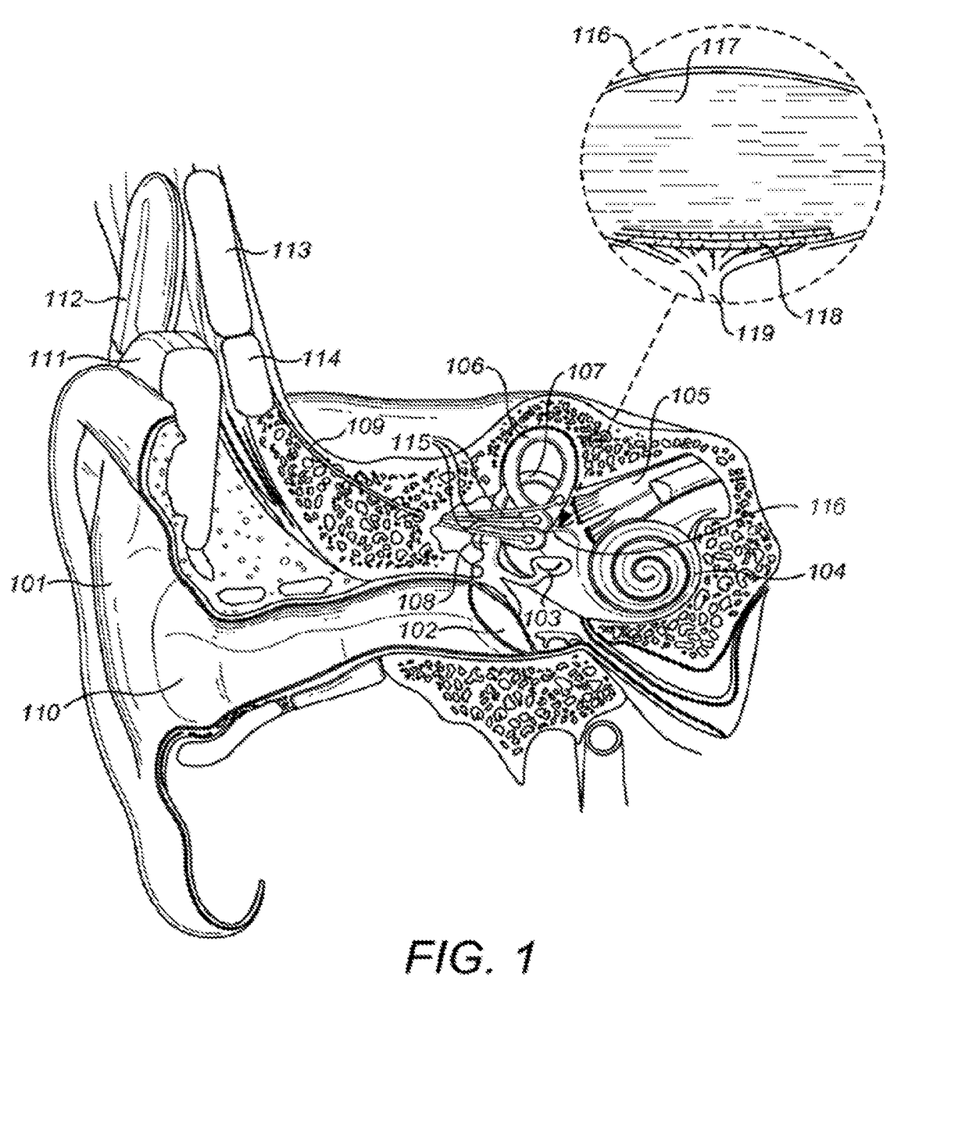
FIG. 1 shows various structures associated with a human ear having a vestibular implant system.

A normal ear directs sounds as shown in FIG. 1 from the outer ear pinna 101 through the generally cylindrical ear canal 110 to vibrate the tympanic membrane 102 (eardrum). The tympanic membrane 102 moves the bones of the middle ear 103 (malleus, incus, and stapes) that vibrate the cochlea 104, which in turn functions as a transducer to generate electric pulses to the brain that are interpreted as sounds.

The balance sensing functionality of the brain also is developed based on neural signals from the vestibular structures of the inner ear, one on each lateral side of the body. The balance sensing vestibular system involves the vestibular labyrinth, its three interconnected and mutually orthogonal semi-circular canals: the superior (anterior) canal 106, posterior canal 107, and horizontal (lateral) canal 108—which sense rotational movement, as well as the macular organs 116 in the utricle and saccule, which sense linear movement. The canals 106, 107, 108 and the otolith organs 116 of the vestibular labyrinth contain hair cells 118 in a viscous endolymph 117 that sense head orientation and head movements, thereby activating vestibular nerve fibers 119 that send an electrical balance signal to the brain 105.

When the head is stationary, the vestibular system generates neural activity at a certain rate that is transmitted by the vestibular nerve to the brain. When the head moves in a given direction, the vestibular system changes the neural activity rate on the affected nerve branch of the vestibular nerve which correlates with the head movement. Unfortunately some people suffer from damaged or impaired vestibular systems or from various diseases that affect intact vestibular systems such as Meniere's disease. Dysfunction of the vestibular system can cause problems such as unsteadiness, vertigo (feeling of rotation) and unsteady vision. To treat such problems, electrical stimulation of the vestibular system can help to restore the balancing function, and vestibular implants are currently under development to provide such an artificial balance signals.

FIG. 1 also shows some components of a vestibular implant system such as are described in U.S. Pat. No. 8,751,012 (incorporated herein by reference in its entirety). An external movement signal (from one or more gyroscopes and/or linear accelerometers not shown) is processed by an external processor 111 to produce an implant communication signal that has an electrical power component and a signal component based on the external movement signal. An external transmitter coil 112 couples the implant communication signal through the skin to an implanted receiver coil 113. Implanted vestibular stimulator 114 then delivers a stimulation signal developed from the signal component through an electrode lead 109 to vestibular stimulator electrodes 115 that electrically stimulate target neural tissue such as the semicircular canals 106, 107, 108, one or both otolith organs, and/or the vestibular nerve 105 or ganglion for vestibular sensation by the patient as a balance signal.

For safety reasons, it is important that the externally worn unit including the motion sensor is always placed in a known, correct orientation when driving the implant. Otherwise the sensor's misaligned input to signal processing, and ultimately to the neural stimulation sites, will lead to a mismatch between real and perceived head movement. Under specific circumstances this may cause a patient to fall and possibly result in injury. This is of special relevance when the implant is located on the head such that sometimes the patient cannot visually observe placing the external unit over the implant.

The correct placement of an external components relative to the implanted portion is currently solved for cochlear implants and other auditory implants by a pair of axially magnetized magnets. One magnet is placed in the center of the implant's receiver coil. The other magnet is placed in the center of the sender coil in the external unit. While placing the external unit's magnet in proximity to that of the implant, the magnetic attraction force causes the external coil to be placed over the implant's coil in a concentric orientation. But there is a remaining degree of freedom in that the external unit can be turned in the radial direction a full 360 degrees relative to the implant. Due to this degree of radial rotation freedom, this solution is not appropriate for placing an external sensor as part of a vestibular implant system.

The external motion sensor may specifically be, for example, a three-axis gyroscope+ three-axis accelerometer configured to measure head angular velocities in terms of three orthogonal axes. Those measurements then are adapted to match the coordinate system of the semi-circular canals (SCCs) through a transformation matrix. The sensor is fixed to the head by the same magnets that keep the transmitting and receiving coils aligned. Therefore it is possible for the external coil to experience rotations on the normal axis to the coil plane. These rotations produce a change on the coordinate system of the motion sensor that leads to a misalignment with the SCCs coordinate system.

Current vestibular implant systems avoid those undesirable rotations via multiple magnet fixation arrangements such as described in U.S. Pat. No. 9,144,677 (incorporated herein by reference in its entirety). That in turn disadvantageously increases the size of the implanted and external parts of the system. Another different solution to this problem involves transcutaneous fixation to the patient's mastoid bone and then extra fixation with a hat or headband, but that clearly is not always convenient. Percutaneous fixation through the skin is also used but that is well-known as a source of irritations and infections.

SUMMARY

Embodiments of the present invention are directed to a portion of a vestibular prosthesis system that includes an external coil housing having a skin interface surface that is configured to lie against the skin of a patient's head behind the outer ear. An external holding magnet is contained within the external coil housing and configured to cooperate with a corresponding implant holding magnet that is located under the skin to securely hold the skin interface surface against the skin over the implant holding magnet. One or more external movement sensors is contained within the external coil housing and is configured to generate an external movement signal representing movement of the patient's head. An external signal processor is in communication with the external movement sensor and is configured for producing an implant communication signal that has an electrical power component and a signal component based on the external movement signal. An external communications coil arrangement is in communication with the external signal processor and is contained within the external coil housing in a plane around the external holding magnet and is configured to cooperate with a corresponding implant communications coil arrangement located under the skin for transcutaneous inductive coupling of the implant communications signal between the external communications coil and the implant communications coil. In such an arrangement, the external coil housing and the external holding magnet are configured to allow rotation of the external coil housing around a rotation axis that passes through the external holding magnet orthogonal to the skin interface surface. The external communications coil arrangement comprises three or more external coil segments that are rotationally adjacent to each other around the rotation axis, where each external coil segment is independently operable by the external signal processor for coupling the implant communication signal. And the external signal processor is configured to periodically operate multiple external coil segments to quantify rotation of the external coil housing and adjust the signal component of the implant communication signal to offset the quantified rotation.

The implant communications coil arrangement also may specifically have three or more implant coil segments rotationally adjacent to each other around the rotation axis, where each implant coil segment is independently operable for coupling the implant communication signal. For example, the implant communications coil arrangement may be configured to sequentially operate two of the implant coil segments while coupling the implant communication signal when the external signal processor quantifies rotation of the external coil housing. In that case, the external signal processor may measure power consumption in each of the external coil segments when quantifying rotation of the external coil housing. The external signal processor may sequentially operate two or more of the external coil segments while coupling the implant communication signal when quantifying rotation of the external coil housing. Or the external signal processor may simultaneously operate all of the external coil segments and all of the implant coil segments while coupling the implant communication signal when quantifying rotation of the external coil housing.

In specific embodiments, the external signal processor may use a coordinate transform matrix to quantify rotation of the external housing. The external coil segments may have different shapes and/or sizes, or they all may have equally matching shapes and sizes.

BRIEF DESCRIPTION OF THE DRAWINGS

FIGS. 3A-3B show how rotation of the external device misaligns the coil segments.

DETAILED DESCRIPTION

Embodiments of the present invention are directed to an improved technique for connecting the external coil in a vestibular implant system that allows natural angular rotation of the external coil, detects such rotations and modifies the communications signal transmitted to the implant to account for such rotations. This results in a reduced size of the implant and external processor compared to conventional arrangements based on multiple magnet fixation. With the reduction in size, the skin contact area also is reduced, decreasing one source of skin irritation. In addition, the external device weighs less compared to the multiple magnet fixation approach, which allows a reduction of the holding magnet and avoids irritation and pressure on the skin. In addition, there is no need for a hat, headband or similar thing to keep the external processor in place.

Figure 2:
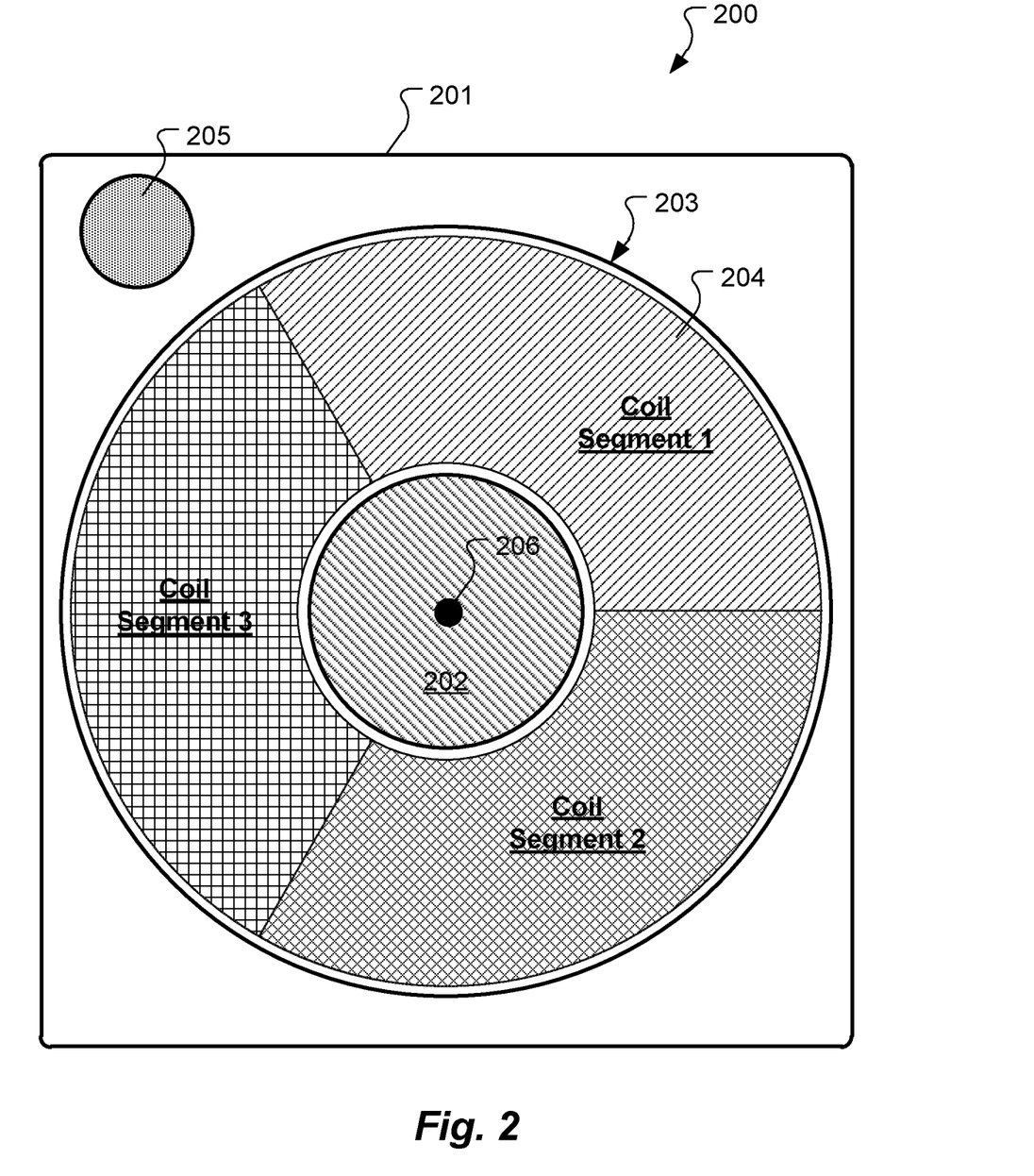
FIG. 2 shows one specific example of an external device for a vestibular prosthesis system according to an embodiment of the present invention.

FIG. 2 shows an external device 200 for a vestibular implant system that includes an external coil housing 201 having a skin interface surface (the bottom plane of the figure under the depicted structures) that is configured to lie against the skin of a patient's head behind the outer ear. An external holding magnet 202 is contained within the external coil housing 201 and is configured to cooperate with a corresponding implant holding magnet that is located under the skin to securely hold the skin interface surface against the skin over the implant holding magnet. One or more external movement sensors 205 are contained within the external coil housing 201 and are configured to generate an external movement signal representing movement of the patient's head. An external signal processor (e.g., 111 in FIG. 1) is in communication with the external movement sensor 205 and is configured for producing an implant communication signal that has an electrical power component and a signal component based on the external movement signal.

An external communications coil arrangement 203 is in communication with the external signal processor 111 and is contained within the external coil housing 201 in a plane around the external holding magnet 202 and is configured to cooperate with a corresponding implant communications coil arrangement located under the skin for transcutaneous inductive coupling of the implant communications signal between the external communications coil and the implant communications coil. In such an arrangement, the external coil housing 201 and the external holding magnet 202 allow rotation of the external coil housing 201 around a rotation axis 206 that passes through the external holding magnet 202 orthogonal to the skin interface surface.

The external communications coil arrangement 203 comprises three or more external coil segments 204 that are rotationally adjacent to each other around the rotation axis 206, where each external coil segment 204 is independently operable by the external signal processor 111 for coupling the implant communication signal. The implant communications coil arrangement in the implant (not shown) is arranged with similar corresponding coil segments. The external signal processor 111 is configured to periodically operate one or more external coil segments 204 to quantify rotation of the external coil housing 201 and adjust the signal component of the implant communication signal to offset the quantified rotation. The coil segments 203 may have the same size and shape, or they may be different in size and shape in order to optimize system behavior in terms of accuracy and power efficiency. Possible examples include, increasing the number of same-sized coils to achieve a better discrimination between them or dividing the functionality of the coils by using any of the coil systems described above solely to measure the rotation and introducing another coil around it responsible for power supply and communication transfer. These and other obvious modifications are intended to be covered by the appended claims.

For normal stimulation only one of the external coil segments 203 and the corresponding implant coil segment may be active and communicate the implant communication signal. It is however understood that the invention is not limited in this respect, for example multiple coil segments 203 may be active to communicate the implant communication signal. Further there may be one coil segment 203 active to communicate the communication signal to the implant and another coil segment 203 to provide energy to the implant. Periodically, the external signal processor 111 will direct the implant to activate two coil segments one after the other to send an inductive signal through them. In this context, sending an inductive signal is understood to include both, generating actively an inductive field by the respective coil segments 203 or by means of load modulation. While one implant coil segment is activated, the external signal processor 111 checks the phase shift of the received signal (and/or the power content in case of actively generated inductive field or consumption in case of load modulation) in each of the external coil segments 203. After that the external signal processor 111 activates another implant coil segment and repeats the measurements. With that information, the external signal processor 111 can determine the rotation of the external coil housing 201 relative to the implant and then adapt a transformation matrix (e.g. by using an elemental rotation matrix) to align the external 201 motion sensor with the rotation axis 206.

Figure 3A:
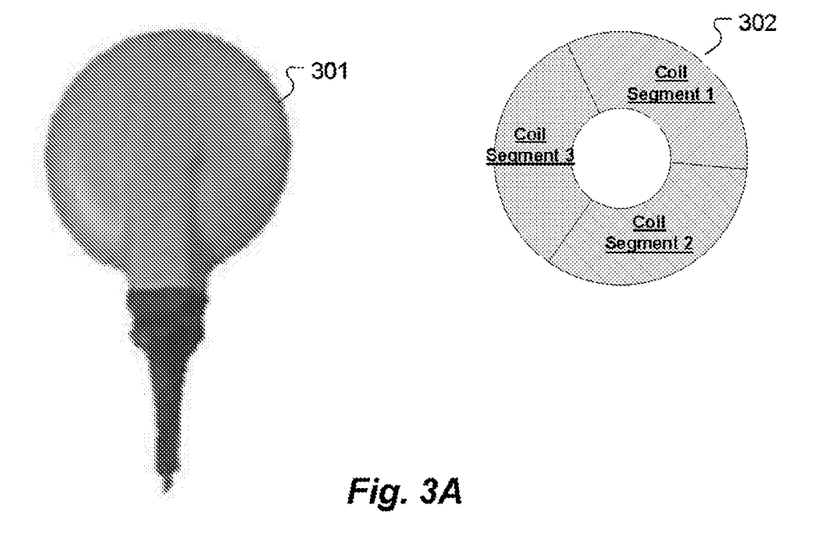

For example, as shown in FIG. 3A, when the external coil housing 301 is correctly aligned with the implant, then the corresponding external and implant coil segments 302 are also correctly aligned. Then if the external signal processor 111 directs the implant Coil Segment 1 to be stimulated, maximum power will be measured in the external Coil Segment 1. If the external coil housing 301 rotates, as shown in FIG. 3B, the external and implanted coil segments 302 are no longer aligned. If then the external signal processor 111 directs the implant Coil Segment 1 to be stimulated, the power measured in the external Coil Segment 1 will decrease and it will increase in external Coil Segment 2 and/or external Coil Segment 3. Depending on those variations of power, the external signal processor 111 then calculates the rotational position of the external coil housing 301 and adjusts the signal transformation matrix in the same manner as described above.

Figure 4:
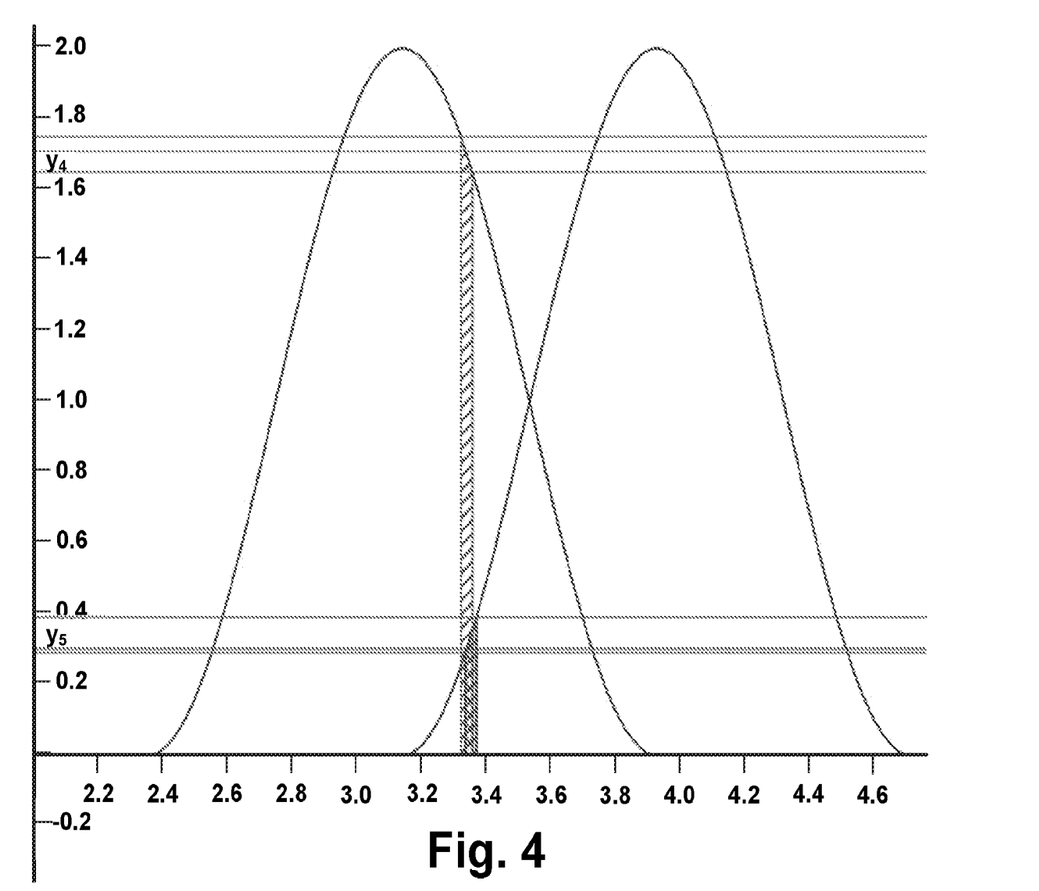
FIG. 4 shows one specific example of the power measurement in an eight coil system in regards to the relative rotation angle.

To calculate the rotation angle for a 3-coil system as described above, the following procedure can be applied. This procedure also works for any number of n given coils, as long as n is greater than 2 and all coil segments 302 have the same shape. Thus, a general formulation is provided. To uniquely calculate the rotation angle of a n-coil system only a number of n−1 coils need to be measured. The power measurements on each coil with respect to the rotation angle can be visualized by plotting the following function for $\alpha \in [0, 2\pi]$ and k=1, ..., n−1, as seen in FIG. 4 for n=8:

$$y_k(\alpha) = \begin{cases} \left(\cos\left(\frac{n\alpha}{2}\right) + 1\right) * \chi_{\left[\frac{2\pi}{n}(k-1), \frac{2\pi}{n}(k+1)\right]}(\alpha), & k \text{ even} \\ \left(\cos\left(\frac{n\alpha}{2} - \pi\right) + 1\right) * \chi_{\left[\frac{2\pi}{n}(k-1), \frac{2\pi}{n}(k+1)\right]}(\alpha), & k \text{ uneven} \end{cases}$$

The resulting array containing the power measurements $y_1, \ldots, y_{n-1}$ has exactly 2 non-zero values. Each of these power measurements provides two possible angles $\alpha_{k,1}$ and $\alpha_{k,2}$. The resulting angle $\alpha$ is the one that both coils have in common. For a given power measurement $y_k$ the angles mentioned above can be calculated as follows:

$$\alpha_{k,1} = \arccos(y_k - 1)\frac{2}{n} + \frac{2\pi}{n}(k-1)$$

$$\alpha_{k,2} = \alpha_{k,1} + \frac{2\pi}{n}$$

$$\alpha \in \{\alpha_{i,1}, \alpha_{i,2}\} \cap \{\alpha_{j,1}, \alpha_{j,2}\},$$

$$\text{for } y_i, y_j \neq 0$$

It is understood that the above procedure is formulated to provide an exact measurement, meaning that physical limitations in the measurement resulting in noise need to be considered to adapt the procedure accordingly. This would mean changing the definition of "non-zero" values to values greater than a certain noise level, and changing the definition of an angle $\alpha$ lying in the intersection of two sets to an angle $\alpha$ lying in a given area around the calculated angles $\alpha_{i,1}$, $\alpha_{i,2}$ and $a_{j,1}$, $a_{j,2}$ whereas the area depends on the noise level. In the case of a system with differently sized coil segments 302, the procedure needs to be adapted accordingly.

Alternatively, in some embodiments, the external signal processor may use one of the external coil segments for stimulation of the implant, and then measure the external coil current and phase, repeating this measurement for each external coil segment while one selected implant coil segment is used to couple the implant communication signal to the implant. These measurements may be repeated for each of the implant coil segments. In another specific embodiment, an internal coil segment can be shorted to achieve a pronounced difference in external coil currents. Or, instead of measuring the primary coil current and phase the implant measures the coil voltages on all three coils and transmits the values digitally to the external system.

Embodiments of the present invention such as those described above provide real-time online tracking and correction of the rotational position of the external coil housing. In existing conventional solutions, by contrast, if the external coil housing is placed incorrectly, the user must realize that as no processing correction is possible. With the automatic detection as described above, the user does not need to carefully ensure correct rotational placement of the external coil housing over the implant. In addition, the external signal processor always knows which of the coil segments is best aligned, and so can increase the efficiency of the inductive link. Also, compatibility with user MRI is better than for conventional multiple magnet solutions.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although various exemplary embodiments of the invention have been disclosed, it should be apparent to those skilled in the art that various changes and modifications can be made which will achieve some of the advantages of the invention without departing from the true scope of the invention.

What is claimed is:

1. A portion of a vestibular prosthesis system comprising:
    an external coil housing having a skin interface surface configured to lie against the skin of a patient's head behind the outer ear;
    an external holding magnet contained within the external coil housing and configured to cooperate with a corresponding implant holding magnet located under the skin to securely hold the skin interface surface against the skin over the implant holding magnet;
    one or more external movement sensors contained within the external coil housing and configured to generate an external movement signal representing movement of the patient's head;
    an external signal processor in communication with the external movement sensor configured for producing an implant communication signal having an electrical power component and a signal component based on the external movement signal; and
    an external communications coil arrangement in communication with the external signal processor and contained within the external coil housing in a plane around the external holding magnet and configured to cooperate with a corresponding implant communications coil arrangement located under the skin for transcutaneous inductive coupling of the implant communications signal between the external communications coil and the implant communications coil;
    wherein the external coil housing and the external holding magnet allow rotation of the external coil housing around a rotation axis that passes through the external holding magnet orthogonal to the skin interface surface;
    wherein the external communications coil arrangement comprises three or more external coil segments rotationally adjacent to each other around the rotation axis, each external coil segment being independently operable by the external signal processor for coupling the implant communication signal; and
    wherein the external signal processor is configured to periodically operate a plurality of the external coil segments to quantify rotation of the external coil housing and adjust the signal component of the implant communication signal to offset the quantified rotation.

2. The system according to claim 1, wherein the implant communications coil arrangement comprises three or more implant coil segments rotationally adjacent to each other around the rotation axis, each implant coil segment being independently operable for coupling the implant communication signal.

3. The system according to claim 2, wherein the implant communications coil arrangement is configured to sequentially operate two of the implant coil segments while coupling the implant communication signal when the external signal processor quantifies rotation of the external coil housing.

4. The system according to claim 3, wherein the external signal processor is configured to measure power consumption in each of the external coil segments when quantifying rotation of the external coil housing.

5. The system according to claim 2, wherein the external signal processor is configured to sequentially operate two or more of the external coil segments while coupling the implant communication signal when quantifying rotation of the external coil housing.

6. The system according to claim 2, wherein the external signal processor is configured to simultaneously operate all of the external coil segments and all of the implant coil segments while coupling the implant communication signal when quantifying rotation of the external coil housing.

7. The system according to claim 1, wherein the external signal processor is configured to use a coordinate transform matrix to quantify rotation of the external housing.

8. The system according to claim 1, wherein the external coil segments have different shapes and/or sizes.

9. The system according to claim 1, wherein the external coil segments have equally matching shapes and sizes.

10. A method of operating a vestibular prosthesis system, the method comprising:
    placing an external coil housing having a skin interface surface against the skin of a patient's head behind the outer ear;
    using an external holding magnet contained within the external coil housing and to cooperate with a corresponding implant holding magnet located under the skin to securely hold the skin interface surface against the skin over the implant holding magnet;
    generating an external movement signal representing movement of the patient's head from one or more external movement sensors contained within the external coil housing;
    producing with an external signal processor in communication with the external movement sensor an implant communication signal having an electrical power component and a signal component based on the external movement signal; and
    using an external communications coil arrangement in communication with the external signal processor and contained within the external coil housing in a plane around the external holding magnet to cooperate with a corresponding implant communications coil arrangement located under the skin for transcutaneous inductive coupling of the implant communications signal between the external communications coil and the implant communications coil;

wherein the external coil housing and the external holding magnet are configured to allow rotation of the external coil housing around a rotation axis that passes through the external holding magnet orthogonal to the skin interface surface;

wherein the external communications coil arrangement comprises three or more external coil segments rotationally adjacent to each other around the rotation axis, each external coil segment being independently operable by the external signal processor for coupling the implant communication signal; and wherein the external signal processor is configured to periodically operate a plurality of the external coil segments to quantify rotation of the external coil housing and adjust the signal component of the implant communication signal to offset the quantified rotation.

11. The method according to claim 10, wherein the implant communications coil arrangement comprises three or more implant coil segments rotationally adjacent to each other around the rotation axis, each implant coil segment being independently operable for coupling the implant communication signal.

12. The method according to claim 11, wherein the implant communications coil arrangement is configured to sequentially operate two of the implant coil segments while coupling the implant communication signal when the external signal processor quantifies rotation of the external coil housing.

13. The method according to claim 12, wherein the external signal processor is configured to measure power consumption in each of the external coil segments when quantifying rotation of the external coil housing.

14. The method according to claim 11, wherein the external signal processor is configured to sequentially operate two or more of the external coil segments while coupling the implant communication signal when quantifying rotation of the external coil housing.

15. The method according to claim 11, wherein the external signal processor is configured to simultaneously operate all of the external coil segments and all of the implant coil segments while coupling the implant communication signal when quantifying rotation of the external coil housing.

16. The method according to claim 10, wherein the external signal processor is configured to use a coordinate transform matrix to quantify rotation of the external housing.

17. The method according to claim 10, wherein the external coil segments have different shapes and/or sizes.

18. The method according to claim 10, wherein the external coil segments have equally matching shapes and sizes.

* * * * *